(12) United States Patent
Peter et al.

(10) Patent No.: US 10,308,979 B2
(45) Date of Patent: Jun. 4, 2019

(54) TARGET ENRICHMENT AND LABELING FOR MULTI-KILOBASE DNA

(71) Applicant: Agilent Technologies, Inc., Loveland, CO (US)

(72) Inventors: Brian Jon Peter, Loveland, CO (US); Robert A. Ach, Loveland, CO (US); Zoltan Timar, Loveland, CO (US); Joel Myerson, Loveland, CO (US); Jeffrey Robert Sampson, Loveland, CO (US); Holly Hogrefe, Loveland, CO (US)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 539 days.

(21) Appl. No.: 13/830,408

(22) Filed: Mar. 14, 2013

(65) Prior Publication Data
US 2013/0323725 A1 Dec. 5, 2013

Related U.S. Application Data

(60) Provisional application No. 61/654,605, filed on Jun. 1, 2012.

(51) Int. Cl.
*C12Q 1/68* (2018.01)
*C12Q 1/6813* (2018.01)
*C12Q 1/6806* (2018.01)

(52) U.S. Cl.
CPC ......... *C12Q 1/6813* (2013.01); *C12Q 1/6806* (2013.01)

(58) Field of Classification Search
USPC ......... 435/6.1, 6.11, 91.1, 183, 283.1, 287.1, 435/287.2; 436/94, 501; 536/23.1, 24.3, 536/24.33
See application file for complete search history.

(56) References Cited

U.S. PATENT DOCUMENTS

| | | | | |
|---|---|---|---|---|
| 5,366,877 A * | 11/1994 | Keith | ............... | C12Q 1/6813 435/6.11 |
| 6,013,435 A * | 1/2000 | Nusbaum | ............... | C12Q 1/689 435/6.14 |
| 2002/0137919 A1* | 9/2002 | Fresco | ............... | C12Q 1/6839 536/25.3 |
| 2005/0181394 A1* | 8/2005 | Steemers | ............... | B82Y 30/00 435/6.11 |
| 2007/0087358 A1* | 4/2007 | Ehrlich | ............... | C12Q 1/6886 435/6.12 |
| 2008/0021205 A1* | 1/2008 | Blau | ............... | C07H 19/00 536/23.1 |
| 2009/0291475 A1* | 11/2009 | Lao | ............... | C12Q 1/6848 435/91.2 |
| 2009/0324610 A1* | 12/2009 | Kiyohara | ............... | A61K 48/00 424/158.1 |
| 2010/0330556 A1* | 12/2010 | Peter | ............... | C12Q 1/6809 435/6.1 |
| 2013/0116130 A1* | 5/2013 | Fu | ............... | C12Q 1/6837 506/4 |

OTHER PUBLICATIONS

"Triplex-stranded DNA" from Wikipedia, the free encyclopedia. Printed on Feb. 7, 2015.*
D-loop from Wikipedia, the free encyclopedia. Printed on Feb. 7, 2015.*
Head, et al. "Method for improved Illumina sequencing library preparation using NuGEN Ovation RNA-Seq System. Biotechniques." Nov. 3, 2011, vol. 50, pp. 1-5.
Knierim, et al., "Systematic comparison of three methods for fragmentation of long-range PCR products for next generation sequencing." PLoS One. Nov. 2011, vol. 6, Issue 11, pp. 1-6.
Myllykangas, et al., "Targeted sequencing library preparation by genomic DNA circularization. BMC Biotechnol." Dec. 14, 2011, pp. 1-12.
Parkinson, et al., "Preparation of high-quality next-generation sequencing libraries from picogram quantities of target DNA." Genome Res., Nov. 16, 2011, pp. 1-36.
Rohland, et el., "Cost-effective, high-throughput DNA sequencing libraries for multiplexed target capture." Genome Res. Jan. 20, 2012, pp. 1-21.
Ehrich, et al. A new method for accurate assessment of DNA quality after bisulfite treatment, Nucleic Acids Research, 2007, vol. 35, No. 5, e29, 8 pages.

* cited by examiner

*Primary Examiner* — Frank W Lu

(57) ABSTRACT

This disclosure provides a method comprising: a) clamping the top and bottom strands of a double stranded DNA molecule to produce a duplex in which the top and bottom strands are linked; b) denaturing the duplex to produce a denatured product; and c) renaturing the denatured product in the presence of a labeled oligonucleotide that is complementary to a sequence of nucleotides in the double stranded DNA molecule, thereby producing a D-loop-containing product. Kits for performing the method and products made by the method are also provided.

17 Claims, 8 Drawing Sheets

A. Sequence without hairpin primers

B. Sequence with hairpin primers

Denaturation reannealing

TARGET ENRICHMENT AND LABELING FOR MULTI-KILOBASE DNA

CROSS-REFERENCING

This application claims the benefit of U.S. Provisional application Ser. No. 61/654,605, filed on Jun. 1, 2012, which application is incorporated by reference herein in its entirety.

BACKGROUND

The higher sequence complexity of longer DNA molecules makes complete denaturation and re-annealing steps more difficult to achieve. As such, many state-of-the art analytical methods for the analysis of DNA (such as those that use microarrays, PCR amplification, or next generation sequencing) intentionally fragment DNA targets. However, once the original template DNA is fragmented, accurate assembly of the sequence for highly repetitive regions can be difficult, and long-range haplotype information may be lost. This disclosure provides a robust method to label, select, and/or manipulate longer DNA molecules.

DEFINITIONS

Figure 1:
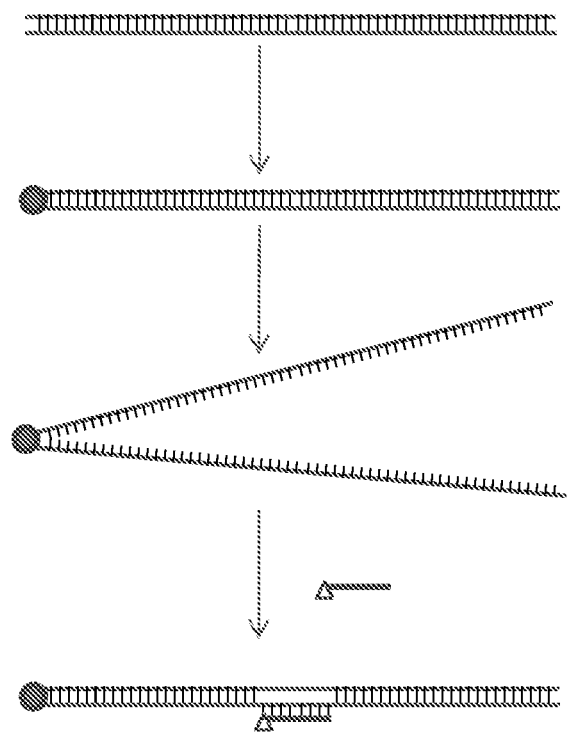
FIG. 1 schematically illustrates certain features of the method. In the embodiment shown in FIG. 1, only one end of the double stranded DNA is shown as being clamped. In practice, either end, both ends or one or more internal positions of the double stranded DNA may be clamped.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

The term "sample" as used herein relates to a material or mixture of materials, typically, although not necessarily, in liquid form, containing one or more analytes of interest.

The term "nucleic acid sample," as used herein denotes a sample containing nucleic acids. A nucleic acid samples used herein may be complex in that they contain multiple different molecules that contain sequences. Genomic DNA from a mammal (e.g., mouse or human) are types of complex samples. Complex samples may have more then $10^4$, $10^5$, $10^6$ or $10^7$ different nucleic acid molecules. A DNA target may originate from any source such as genomic DNA, or an artificial DNA construct. Any sample containing nucleic acid, e.g., genomic DNA made from tissue culture cells or a sample of tissue, may be employed herein.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "nucleic acid sample," as used herein denotes a sample containing nucleic acids.

The term "target polynucleotide," as use herein, refers to a polynucleotide of interest under study. In certain embodiments, a target polynucleotide contains one or more sequences that are of interest and under study.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers. An oligonucleotide may be 10 to 20, 11 to 30, 31 to 40, 41 to 50, 51-60, 61 to 70, 71 to 80, 80 to 100, 100 to 150 or 150 to 200 nucleotides in length, for example.

The term "hybridization" refers to the process by which a strand of nucleic acid joins with a complementary strand through base pairing as known in the art. A nucleic acid is considered to be "Selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions include hybridization at about 42 C in 50% formamide, 5×SSC, 5×Denhardt's solution, 0.5% SDS and 100 ug/ml denatured carrier DNA followed by washing two times in 2×SSC and 0.5% SDS at room temperature and two additional times in 0.1×SSC and 0.5% SDS at 42° C.

The term "duplex," or "duplexed," as used herein, describes two complementary polynucleotides that are base-paired, i.e., hybridized together.

The term "amplifying" as used herein refers to generating one or more copies of a target nucleic acid, using the target nucleic acid as a template.

The terms "determining", "measuring", "evaluating", "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

As used herein, the term "$T_m$" refers to the melting temperature of an oligonucleotide duplex at which half of the duplexes remain hybridized and half of the duplexes dissociate into single strands. The $T_m$ of an oligonucleotide duplex may be experimentally determined or predicted using the following formula $T_m=81.5+16.6(\log_{10} [Na^+])+0.41$ (fraction G+C)−(60/N), where N is the chain length and [Na$^+$] is less than 1 M. See Sambrook and Russell (2001; Molecular Cloning: A Laboratory Manual, 3$^{rd}$ ed., Cold Spring Harbor Press, Cold Spring Harbor N.Y., ch. 10). Other formulas for predicting $T_m$ of oligonucleotide duplexes exist and one formula may be more or less appropriate for a given condition or set of conditions.

The term "free in solution," as used here, describes a molecule, such as a polynucleotide, that is not bound or tethered to another molecule.

The term "partitioning", with respect to a genome, refers to the separation of one part of the genome from the remainder of the genome to produce a product that is isolated from the remainder of the genome. The term "partitioning" encompasses enriching.

The term "genomic region", as used herein, refers to a region of a genome, e.g., an animal or plant genome such as the genome of a human, monkey, rat, fish or insect or plant. In certain cases, an oligonucleotide used in the method described herein may be designed using a reference genomic region, i.e., a genomic region of known nucleotide sequence, e.g., a chromosomal region whose sequence is deposited at NCBI's Genbank database or other database, for example. Such an oligonucleotide may be employed in an assay that uses a sample containing a test genome, where the test genome contains a binding site for the oligonucleotide.

The term "genomic sequence", as used herein, refers to a sequence that occurs in a genome. Because RNAs are transcribed from a genome, this term encompasses sequence that exist in the nuclear genome of an organism, as well as sequences that are present in a cDNA copy of an RNA (e.g., an mRNA) transcribed from such a genome.

The term "genomic fragment", as used herein, refers to a region of a genome, e.g., an animal or plant genome such as the genome of a human, monkey, rat, fish or insect or plant. A genomic fragment may be an entire chromosome, or a fragment of a chromosome. A genomic fragment may be adaptor ligated (in which case it has an adaptor ligated to one or both ends of the fragment, to at least the 5' end of a molecule), or non-adaptor ligated.

In certain cases, an oligonucleotide used in the method described herein may be designed using a reference genomic region, i.e., a genomic region of known nucleotide sequence, e.g., a chromosomal region whose sequence is deposited at NCBI's Genbank database or other database, for example. Such an oligonucleotide may be employed in an assay that uses a sample containing a test genome, where the test genome contains a binding site for the oligonucleotide.

The term "sequence-specific restriction endonuclease" or "restriction enzyme" refers to an enzyme that cleaves double-stranded DNA at a specific sequence to which the enzyme binds.

The term "affinity tag", as used herein, refers to moiety that can be used to separate a molecule to which the affinity tag is attached from other molecules that do not contain the affinity tag. An "affinity tag" is a member of a specific binding pair, i.e. two molecules where one of the molecules through chemical or physical means specifically binds to the other molecule. The complementary member of the specific binding pair, referred to herein as a "capture agent" may be immobilized (e.g., to a chromatography support, a bead or a planar surface) to produce an affinity chromatography support that specifically binds the affinity tag. In other words, an "affinity tag" may bind to a "capture agent", where the affinity tag specifically binds to the capture agent, thereby facilitating the separation of the molecule to which the affinity tag is attached from other molecules that do not contain the affinity tag.

As used herein, the term "biotin moiety" refers to an affinity agent that includes biotin or a biotin analogue such as desthiobiotin, oxybiotin, 2'-iminobiotin, diaminobiotin, biotin sulfoxide, biocytin, etc. Biotin moieties bind to streptavidin with an affinity of at least $10^{-8}$M. A biotin affinity agent may also include a linker, e.g., -LC-biotin, -LC-LC-Biotin, -SLC-Biotin or -PEG$_n$-Biotin where n is 3-12.

As used herein, the term "cleavable" in the context of "cleavable bond" refers to a covalent bond in a molecule that can be selectively cleaved to produce two products. Application of a suitable cleavage stimulus to a molecule that contains more than one cleavable bonds that are cleaved by the stimulus will produce more than two products.

The term "terminal nucleotide", as used herein, refers to the nucleotide at either the 5' or the 3' end of a nucleic acid molecule. The nucleic acid molecule may be in double-stranded (i.e., duplexed) or in single-stranded form.

The term "ligating", as used herein, refers to the enzymatically catalyzed joining of the terminal nucleotide at the 5' end of a first DNA molecule to the terminal nucleotide at the 3' end of a second DNA molecule.

A "plurality" contains at least 2 members. In certain cases, a plurality may have at least 10, at least 100, at least 100, at least 10,000, at least 100,000, at least $10^6$, at least $10^7$, at least $10^8$ or at least $10^9$ or more members.

If two nucleic acids are "complementary", each base of one of the nucleic acids base pairs with corresponding nucleotides in the other nucleic acid. The term "complementary" and "perfectly complementary" are used synonymously herein.

The term "digesting" is intended to indicate a process by which a nucleic acid is cleaved by a restriction enzyme. In order to digest a nucleic acid, a restriction enzyme and a nucleic acid containing a recognition site for the restriction enzyme are contacted under conditions suitable for the restriction enzyme to work. Conditions suitable for activity of commercially available restriction enzymes are known, and supplied with those enzymes upon purchase.

A "oligonucleotide binding site" refers to a site to which an oligonucleotide hybridizes in a target polynucleotide.

The term "separating", as used herein, refers to physical separation of two elements (e.g., by size or affinity, etc.) as well as degradation of one element, leaving the other intact.

The term "target genomic fragment" refers to both a nucleic acid fragment that is a direct product of fragmentation of a genome, and also to a nucleic acid fragment of a genome to which adaptors have been added. An oligonucleotide that hybridizes to a target genomic fragment to base-pair to the genome sequence or to the adaptors. A target genomic fragment may be in the range of 1 kb in length to over 500 kb in length or more, e.g., 5 kb to 100 kb, for example.

The term "reference chromosomal region," as used herein refers to a chromosomal region of known nucleotide sequence, e.g. a chromosomal region whose sequence is deposited at NCBI's Genbank database or other database, for example.

The term "strand" as used herein refers to a nucleic acid made up of nucleotides covalently linked together by phosphodiester bonds.

In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. Until they become covalently linked, the first and second strands are distinct molecules. For ease of description, the "top" and "bottom" strands of a double stranded nucleic acid in which the top and bottom strands have been covalently linked will still be described as the "top" and "bottom" strands. In other words, for the purposes of this disclosure, the top and bottom strands of a double stranded to not need to be separated molecules. The nucleotide sequences of the first strand of several exemplary mammalian chromosomal regions (e.g., BACs, assemblies, chromosomes, etc.) is known, and may be found in NCBI's Genbank database, for example.

The term "top strand," as used herein, refers to either strand of a nucleic acid but not both strands of a nucleic acid. When an oligonucleotide or a primer binds or anneals "only to a top strand," it binds to only one strand but not the other. The term "bottom strand," as used herein, refers to the strand that is complementary to the "top strand." When an oligonucleotide binds or anneals "only to one strand," it binds to only one strand, e.g., the first or second strand, but not the other strand. If an oligonucleotide binds or anneals to both strands of a double stranded DNA, the oligonucleotide may have two regions, a first region that hybridizes with the top strand of the double stranded DNA, and a second region that hybridizes with the bottom strand of the double stranded DNA.

The term "double stranded DNA molecule" refers to both double stranded DNA molecules in which the top and bottom strands are not covalently linked, as well as double stranded DNA molecules in which the top and bottom stands are covalently linked. With the exception of certain regions (e.g., a D-loop or the loop regions of a hairpin region) the top and bottom strands of a double stranded are base paired with one other by Watson-Crick interactions.

The term "clamping" refers to any way of linking the strands of a double stranded DNA together such that the strands do not fully separate from one another when they are exposed to denaturing conditions, where the term "denaturing conditions", for the purposes of this definition, refers to incubation in a buffer composed of 20 mM Tris-HCl (pH 8.4) and 50 mM KCl, for 1 minute at 94° C. As will be describe in greater detail below, clamping may be done by directly or indirectly covalently linking the top and bottom strands of a double stranded DNA molecule to another, or by using protein that holds the strands of a double stranded DNA molecule together under denaturing conditions.

The term "covalently linking" refers to the production of a covalent linkage between two separate molecules, e.g., the top and bottom strands of a double stranded nucleic acid.

The term "non-covalently linking" refers to the production of a non-covalent linkage between two separate molecules, e.g., by hydrogen bonds, ionic bonds, van der Waals forces, topological links, and hydrophobic interactions.

The term "covalently linked duplex" refers to a double stranded DNA molecule in which the top strand is covalently linked to the bottom strand. Methods for covalently linking the strands of a duplex are described in greater detail below.

The term "denaturing," as used herein, refers to the separation of at least a portion of the base pairs of a nucleic acid duplex by placing the duplex in suitable denaturing conditions. Denaturing conditions are well known in the art. In one embodiment, in order to denature a nucleic acid duplex, the duplex may be exposed to a temperature that is above the Tm of the duplex, thereby releasing one strand of the duplex from the other. In certain embodiments, a nucleic acid may be denatured by exposing it to a temperature of at least 90° C. for a suitable amount of time (e.g., at least 30 seconds, up to 30 mins). In certain embodiments, fully denaturing conditions may be used to completely separate the base pairs of the duplex. In other embodiments, partially denaturing conditions (e.g., with a lower temperature than fully denaturing conditions) may be used to separate the base pairs of certain parts of the duplex (e.g., regions enriched for A-T base pairs may separate while regions enriched for G-C base pairs may remain paired.) Nucleic acid may also be denatured chemically (e.g., using urea or NaOH).

The terms "renaturing" or "reannealing", as used herein, refer to the formation of an original nucleic acid duplex after it has been denatured. In one embodiment, in order to renature a nucleic acid duplex after it has been denatured, a denatured duplex may be exposed to a temperature that is below the Tm of the duplex, thereby causing one strand of the duplex to base pair with the other. In certain embodiments, a nucleic acid may be renatured by exposing it to a temperature of less than 37° C. for a suitable amount of time (e.g., at least 30 seconds, up to 30 mins). In some cases, a nucleic acid may be renatured by ramping the temperature down from the denaturing temperature (which may be above 90° C.) to a renaturing temperature over a period of time.

The term "labeled oligonucleotide", as used herein, refers to an oligonucleotide that is has an affinity tag (e.g., a biotin moiety,) an oligonucleotide modified with atoms or groups enabling separation or detection (e.g., bromo-deoxyuridine, or colloidal gold particles conferring different density) or an optically detectable label (e.g., a fluorescence or another type of light emitting label). Oligonucleotides that contain only naturally occurring nucleotides are not labeled oligonucleotides.

The term "adaptor" refers to double stranded as well as single stranded molecules. An adaptor can be DNA or RNA, or a mixture of the two. An adaptor made containing RNA may be cleavable by RNase treatment or by alkaline hydrolysis.

The term "adaptor-ligated", as used herein, refers to a nucleic acid that has been ligated to an adaptor. The adaptor can be ligated to a 5' end or a 3' end of a nucleic acid molecule.

The term "adaptor" refers to a nucleic acid that is ligatable to both strands of a double stranded DNA molecule. In one embodiment, an adaptor may be a hairpin adaptor (i.e., one molecule that base pairs with itself to form a structure that has a double stranded stem and a loop, where the 3' and 5' ends of the molecule ligate to the 5' and 3' ends of the double stranded DNA molecule, respectively). In another embodiment, an adaptor may itself be composed of two distinct oligonucleotide molecules that are base paired with one another. As would be apparent, a ligatable end of an adaptor may be designed to compatible with overhangs made by cleavage by a restriction enzyme, or it may have blunt ends.

The term "directly", in the context of a covalent linkage, refers to a linkage that goes directly between one moiety (e.g., a first nucleotide) and another moiety (e.g., the nucleotide based paired with the first nucleotide).

The term "indirectly", in the context of a covalent linkage, refers to a linkage that indirectly joins one moiety and another moiety. For example, two nucleotides that are base paired with one another in a double stranded DNA molecule can be indirectly covalently linked by directly linking two other base paired nucleotides in the same double stranded DNA molecule.

The term "surface-tethered" refers to a molecule that is immobilized on a surface of a solid substrate, where the substrate can have a variety of configurations, e.g., a sheet, bead, or other structure.

The term "genotyping", as used herein, refers to any type of analysis of a nucleic acid sequence, and includes sequencing, polymorphism (SNP) analysis, and analysis to identify rearrangements.

The term "sequencing", as used herein, refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" refers to the so-called parallelized sequencing-by-synthesis or sequencing-by-ligation platforms currently employed by Illumina, Life Technologies, and Roche etc. Next-generation sequencing methods may also include nanopore sequencing methods or electronic-detection based methods such as Ion Torrent technology commercialized by Life Technologies.

The term "displacement loop" or "D-loop" for short refers to a DNA structure in which the two strands of a double-stranded DNA molecule are separated for a region and held apart by a third strand of DNA. The third strand has a sequence (e.g., 10-100 bases, or more) that is complementary to at least one of the strands of the double-stranded DNA molecule and pairs with it, thus displacing the other strand in the region.

Other definitions of terms may appear throughout the specification.

DESCRIPTION OF EXEMPLARY EMBODIMENTS

With reference to FIG. 1, provided herein is a method comprising a) clamping the top and bottom strands of a double stranded DNA molecule to produce a duplex in which the top and bottom strands are linked; b) denaturing the duplex to produce a denatured product; and c) renaturing the denatured product in the presence of a labeled oligonucleotide that is complementary to a sequence of nucleotides in the double stranded DNA molecule, thereby producing a D-loop-containing product.

The "clamping" shown in FIG. 1 is schematically illustrated by a circle that joins one end of the double stranded DNA molecule together. In practice, the clamping may be done at any point along the double stranded DNA molecule, at any preselected or random position, and any number of points. For example, one end or both ends of the double stranded DNA molecule may be clamped, or the clamping may be done at one or more (e.g., 2, 3, 4 or 5-10 or more) internal positions of the double stranded DNA molecule. Further, several different double stranded DNA molecules may be targeted in a single reaction (e.g. at least 5, at least 10, at least 50, at least 100 or at least 1,000 or more), where the different molecules may represent different regions of a genome.

Also as will be described in greater detail below, the clamping may be done by directly or indirectly covalently linking the top and bottom strands of a double stranded DNA molecule to another, or by using a protein (e.g., a thermostable clamping protein) that holds the strands of a double stranded DNA molecule together under denaturing conditions. Using this method, the complementary strands are more able to "find each other" after denaturation, which greatly increases the efficiency of renaturation. Moreover, because the strands are linked prior to denaturation, the complementary strands are paired in a way that reconstitutes the original double stranded DNA molecule.

Although the method may be effectively practiced on any double stranded DNA that is greater than 1 kb in length, the method finds particular utility when practiced on longer DNA molecules that are of, e.g., 5 kb to 200 kb, or longer. For example, the double stranded DNA used in the method may a fragment of a genome that is in the range of 5 kb to 10 kb, 10 kb to 50 kb or 50 kb to 200 kb in length, or longer. Such fragments may be made by fragmenting a genome using physical methods (e.g., sonication, nebulization, or shearing), chemically, or enzymatically (e.g., using a rare-cutting restriction enzyme).

In some embodiments, the clamping comprises covalently linking the top and bottom strands of the double stranded DNA molecule to produce duplex in which the top and bottom strands are covalently linked, either directly or indirectly. This may be done using any of a number of different methods. Several concepts are discussed below in the context of ligating a hairpin adaptor to a double stranded DNA molecule. These concepts can be generalized the other methods.

Figure 2:
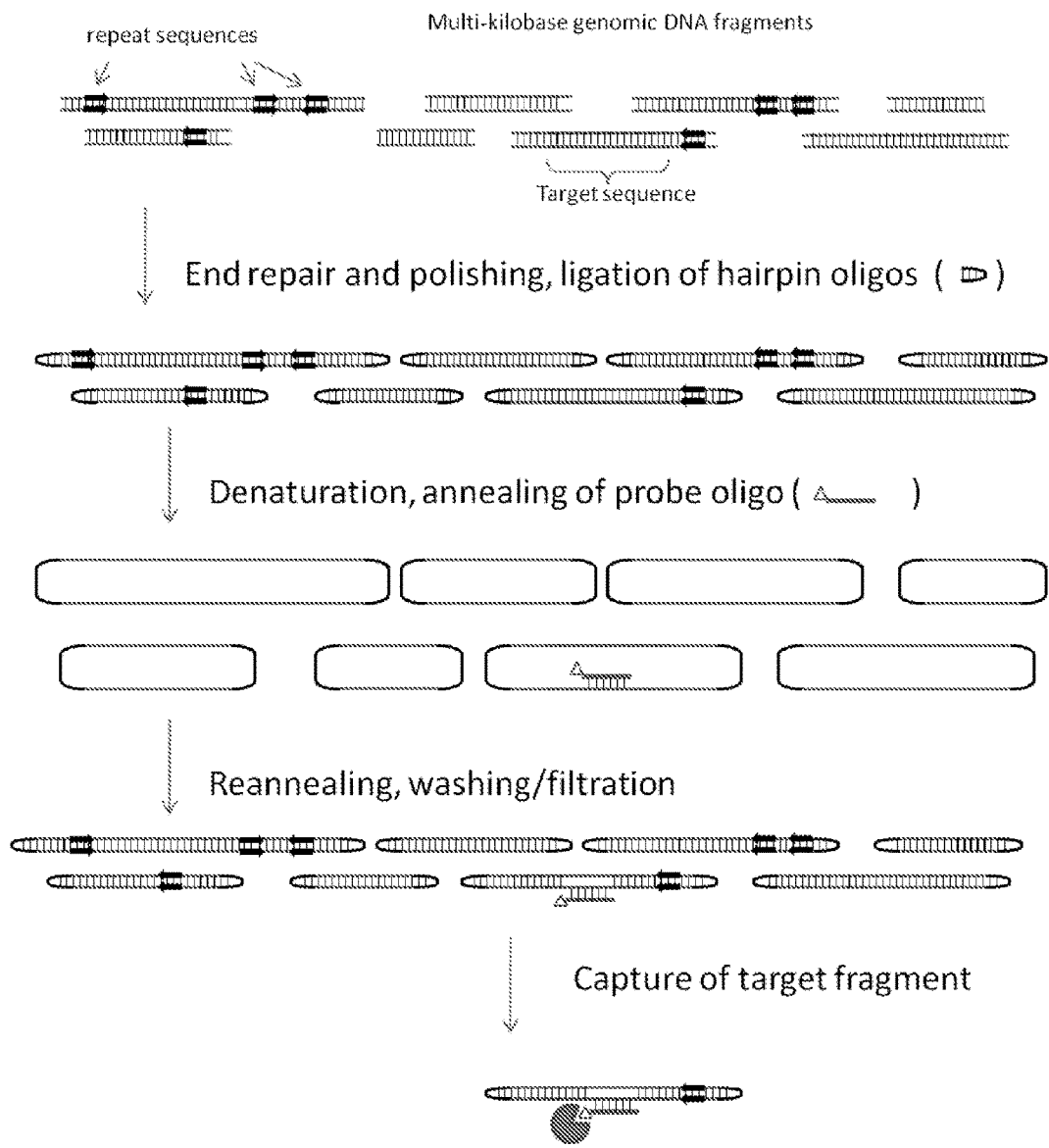
FIG. 2 provides an outline of one embodiment of the method.

For example, in one embodiment, the covalently linking may be done by ligating a hairpin adaptor to one or both ends of the double stranded DNA. An outline of the method is shown in FIG. 2. In this embodiment, genomic DNA may be lightly sheared, or digested with a rare-cutting enzyme, to create fragments on the order of 20-200 kilobases. In order to enable ligation, the ends of the DNAs can be filled in with Klenow fragment polymerase, treated with polynucleotide kinase, and A-tailed. Next, adapter primer oligos are ligated to the genomic DNA. Methods for DNA end repair and adaptor ligation are known in the art. The adaptors used in this embodiment are composed of a single strand of DNA with a palindromic sequence that creates a hairpin. When the adapters are ligated to linear duplex DNA, the top and bottom strands are covalently joined at their ends, creating a single stranded DNA circle. Even if only one adapter ligates, the top and bottom strands are still covalently bound, and thus each strand should anneal with its exact complement after denaturation.

After the two strands are covalently joined, the DNA fragments can be denatured and reannealed in a way that reconstitutes the original top and bottom strand pairing in the double stranded DNA molecule. After partial or full denaturation, one or more labeled oligonucleotides can be added, which should bind to their complementary sequences. The DNA can reanneal, and unbound labeled oligonucleotide can be removed by any suitable means.

Figure 7:
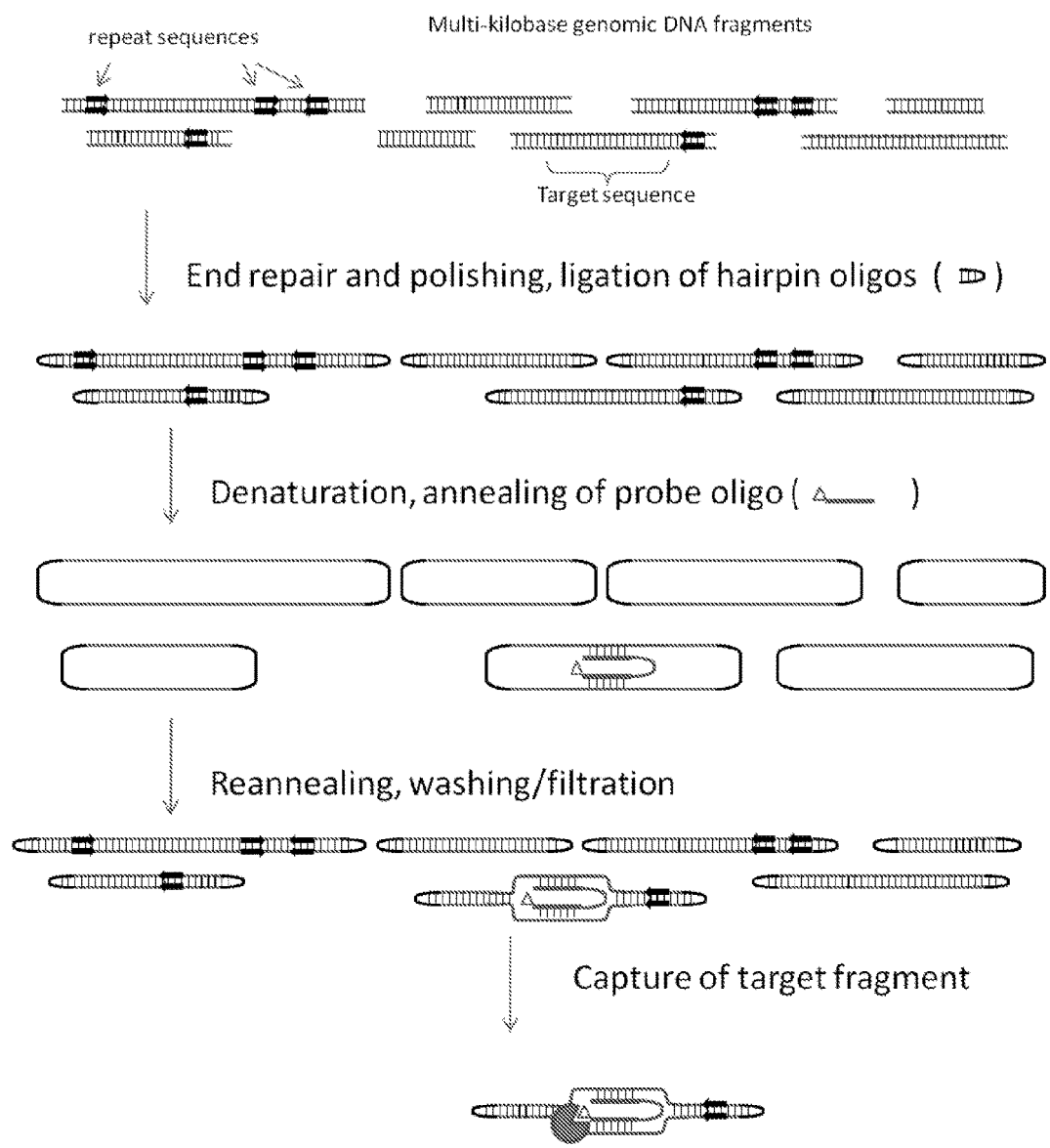
FIG. 7 schematically illustrates an embodiment in which a double stranded DNA molecule is captured using a single capture oligonucleotide that hybridizes to both strands of the double stranded DNA molecule.

After reannealing the target DNA should contain a triplex with the hybridization probe bound. As noted above, labeled oligonucleotide may be used to fluorescently label the target DNA (see, e.g., FIG. 5), or as a capture agent (FIG. 2). In certain embodiments, the labeled oligonucleotide may be designed to include locked nucleic acid (LNA) in order to enhance the stability of the triplex. Alternatively, both the top and bottom strands of the target DNA could be targeted using a labeled oligonucleotide containing unstructured nucleic acid (UNA) bases. FIG. 7 illustrates a method that uses a labeled oligonucleotide that hybridizes to both strands of a target nucleic acid.

Figure 4:
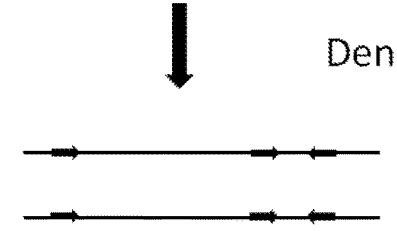
FIG. 4 schematically illustrates an embodiment that uses GC rich hairpin primers to facilitate correct alignment of repeats during reannealing.
Figure 4:
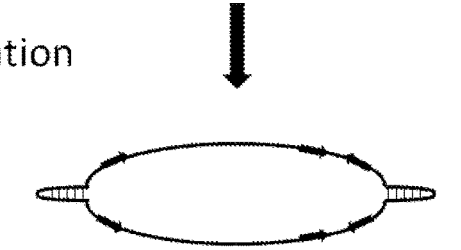
Figure 4:

In particular cases, the adaptor may comprises a hairpin region that has a $T_m$ of over 70° C. (e.g., a Tm of at least 80° C., at least 90° C., at least 95° C. or at least 100° C.) and in certain cases may contain an "unmeltable hairpin" such as that described in e.g., Varani et al (*Exceptionally stable nucleic acid hairpins* Annu Rev Biophys Biomol Struct. 1995; 24:379-404). In a particular cases, a hairpin adaptor may contain the sequence d(GCGAAGC) (SEQ ID NO:1), which forms very a stable hairpin with a melting temperatures of above 70° C. (Padtra et al *Refinement of d(GC-GAAGC)* (SEQ ID NO:1) *hairpin structure using one-and two-bond residual dipolar couplings* J. Biomol. NMR. 2002 24:1-14). Such a hairpin sequence could be extended to include other useful sequences (such as a restriction site, allowing cleavage of the hairpin, or a sequencing primer binding site or a PCR primer binding site, etc.), but could serve to nucleate the renaturation of the DNA duplex (see. e.g., FIG. 4). In an alternative embodiment, one could use hairpin primers with long, GC rich sequences. These sequences would be the last to denature, and the first to renature, and this action could help align the repeats of long DNA molecules in the correct register (see, e.g., FIG. 4). Finally, in certain cases, one could use a hairpin adaptor that contains interstrand crosslinks that would prevent denaturation of the hairpin. By using these methods or a combination of them, it should be possible to partially denature the target duplex without denaturing the hairpin primers, allowing hybridization of the labeled oligonucleotide, while preserving the correct pairing and register of the top and bottom strands.

In some embodiments, the covalently linking may be done by ligating a double stranded adaptor (i.e., an adaptor composed of two oligonucleotides that are annealed together; not a hairpin adaptor) to one or both ends of the double stranded DNA, and covalently cross-linking the top and bottom strands of the double stranded adaptor. Such cross-linking may be done using methods that are known in the art, e.g., by synthesizing a pair of complementary oligonucleotides, where one a reactive group (e.g., an amine), and the other contains a moiety that reacts with the reactive group (e.g., an NHS ester). The oligonucleotides can be allowed to anneal, and then linked together by a reaction between the reactive group and the moiety. Alternatively, HMT [4'-(hydroxymethyl)-4,5',8-trimethylpsoralen] can be attached to a thymidine residue in an oligo and reacted to a complementary oligonucleotide to create a duplex with a single interstrand crosslink, as described by Shi and Hearst (Biochemistry 1987 26: 3792-3798). Further exemplary linking groups and methods of using the same are described in Hermanson, "Bioconjugate Techniques" 2nd Edition, Academic Press, 2008. Alternatively one could cross-link modified thymidines using the method of Glick et al, J. Org. Chem. 1991 56: 6746-6747).

Figure 6:
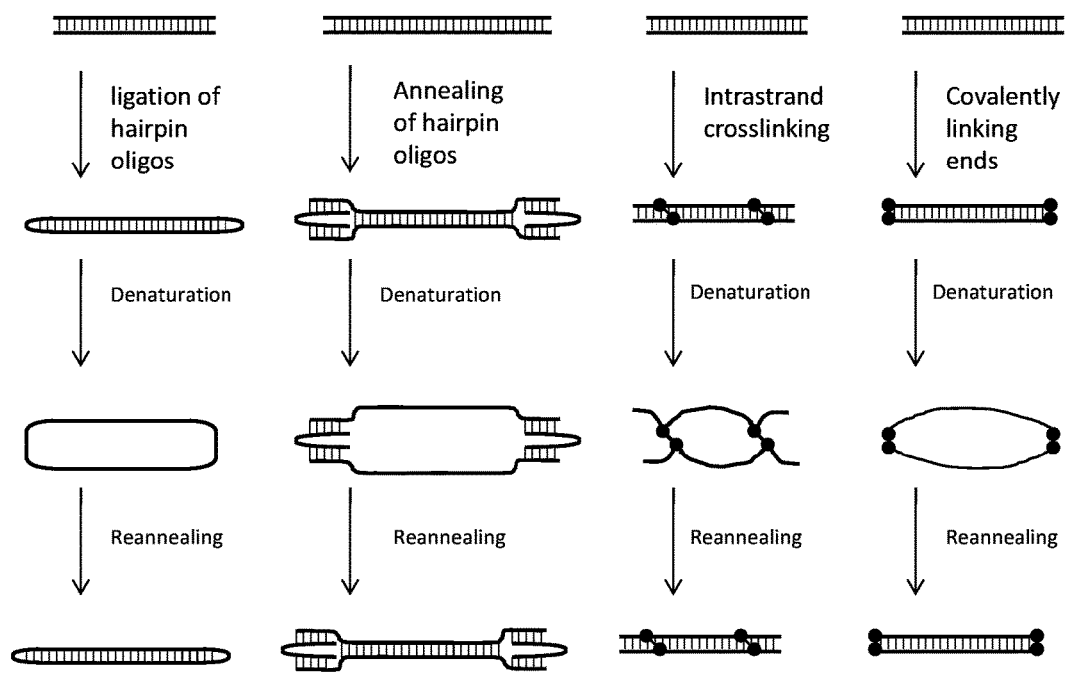
FIG. 6 schematically illustrates different methods for clamping the top and bottom strands of a double stranded DNA molecule together.

In certain cases, the covalently linking is done by covalently linking the top and bottom strands of the double stranded DNA molecule to one another directly. For example, the double stranded DNA could be sparsely cross-linked with psoralen (e.g., to produce, e.g., one or more cross-linking events every 500 bp to 10 kb). In other embodiments, the covalently linking may be done using known coupling agents such as CNBr plus imidazole and a divalent metal, N-cyanoimidazole with $ZnCl_2$, 1-(3-dimethylaminopropyl)-3 ethylcarbodiimide HCl, and other carbodiimides and carbonyl diimidazoles. This embodiment and other methods for clamping the strands of a double stranded DNA together are schematically illustrated in FIG. 6.

In another embodiment, the covalently linking may be done by cross-linking by adding a terminal nucleotide that comprises a linking moiety to the top or bottom strand of the double stranded DNA molecule, and then reacting the linking moiety with the other strand of the double stranded DNA molecule. In this embodiment, the target DNA can be digested using a restriction enzyme that leaves a 5' overhang terminating with a phosphate. The recessed 3' OH end can be extended by adding a polymerase and a modified nucleotide that carries a chemical modification to the base. For example, amino-allyl nucleotides could be used to produce a reactive amine group at the 3' end. This group could be coupled to the 5' terminal phosphate, covalently linking to the top and bottom strands of the DNA. In another embodiment, the modified nucleotide that is incorporated may contain a photoreactive nucleotide analog (see, e.g., Bartholomew et al, Methods Mol. Biol. 2009 543: 453-74). In one embodiment, the target DNA is digested (e.g., using NotI) to produce a 5' overhang, a DNA polymerase (e.g., Klenow) is added to link a modified nucleotide (e.g., containing a 5-carboxythymine) to the 3' end of the target DNA, the 5' phosphate can be modified using EDC, imidazole and ethylenediamine to convert 5' phosphate to phosphoramidate, and the amino terminus off of the 5' phosphoramidate can be cross-linked with the added modified nucleotide.

In some embodiments, the adaptor may comprise at least one cleavable linkage so that it can be removed from the D-loop-containing product, e.g., after the D-loop-containing product has been isolated. Suitable cleavable bonds that may be employed include, but are not limited to, the following: base-cleavable sites such as esters, particularly succinates (cleavable by, for example, ammonia or trimethylamine), quaternary ammonium salts (cleavable by, for example, diisopropylamine) and urethanes (cleavable by aqueous sodium hydroxide); acid-cleavable sites such as benzyl alcohol derivatives (cleavable using trifluoroacetic acid), teicoplanin aglycone (cleavable by trifluoroacetic acid followed by base), acetals and thioacetals (also cleavable by trifluoroacetic acid), thioethers (cleavable, for example, by HF or cresol) and sulfonyls (cleavable by trifluoromethane sulfonic acid, trifluoroacetic acid, thioanisole, or the like); nucleophile-cleavable sites such as phthalamide (cleavable by substituted hydrazines), esters (cleavable by, for example, aluminum trichloride); and Weinreb amide (cleavable by lithium aluminum hydride); and other types of chemically cleavable sites, including phosphorothioate (cleavable by silver or mercuric ions) and diisopropyl-dialkoxysilyl (cleavable by fluoride ions). Other cleavable bonds will be apparent to those skilled in the art or are described in the pertinent literature and texts (e.g., Brown (1997) Contemporary Organic Synthesis 4(3); 216-237). In particular embodiments, a photocleavable linker (e.g., a uv-cleavable linker) may be employed. Suitable photocleavable linkers for use in may include ortho-nitrobenzyl-based linkers, phenacyl linkers, alkoxybenzoin linkers, chromium arene complex linkers, NpSSMpact linkers and pivaloylglycol linkers, as described in Guillier et al (Chem. Rev. 2000 Jun. 14; 100(6):2091-158).

Figure 9:
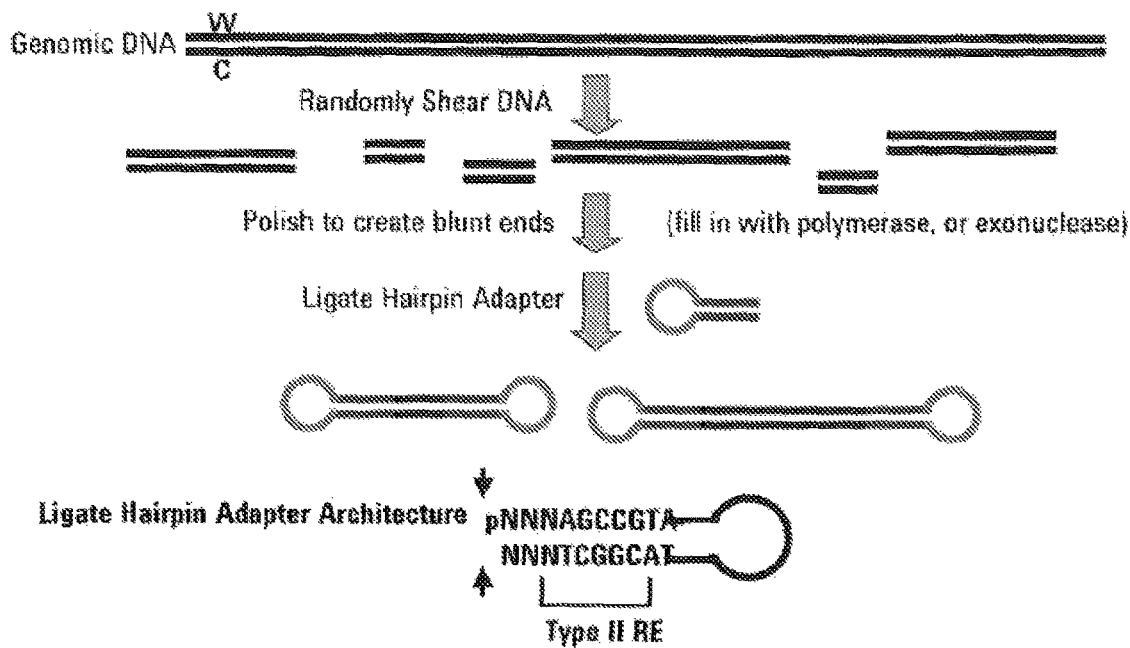
FIG. 9 schematically illustrates an embodiment in which specific adapter sequences facilitate cleavage of adapter dimer molecules by a restriction endonuclease.

In particular embodiments, the adaptor ligated to the ends of the genomic DNA may be made of RNA. Ligation to the ends of the genomic DNA would be accomplished using T4 RNA ligase. The advantage of using RNA hairpins would be that once the desired fragments of genomic DNA were isolated, the hairpins could be removed by RNase treatment or by alkaline hydrolysis, yielding the original genomic DNA fragment. In addition, if RNA capture probes were used, these would also be degraded by the same treatment, again yielding only the purified genomic DNA. Other cleavable linkages are known. In particular cases (and as illustrated in FIG. 9) the adaptor used may comprise a nucleotide sequence that produces a restriction site, e.g., a Type II site, if primer dimers are produced. After ligation, the primer dimers can be digested to produce a ligatable end that can be re-ligated to the fragments.

In certain cases, the clamping comprises non-covalently linking the top and bottom strands of the double stranded DNA molecule using a protein that holds the top and bottom strands together. In some embodiments, this may be done using a "DNA clamp" protein (also known as a "sliding clamp"), which is a protein fold that serves as a processivity-promoting factor in DNA replication. In bacteria, the beta subunit of pol III (associated with DNA polymerase III) acts as a DNA clamp. In archaea, PCNA (associated with pol c) acts as a DNA clamp, in eukaryotes, PCNA (associated with DNA polymerase delta) acts as a DNA clamp, and in viruses, gp43/gp45 (which is part of RB69 Pol/T4 Pol) acts as a DNA clamp. Thermostable DNA clamps (i.e., DNA clamps that are stable under the denaturation conditions used), are obtainable from thermophilic organisms or by modifying non-termostable DNA clamps. See, e.g., Kitabayashi et al (Biosci. Biotechnol. Biochem 2002 66: 2194-2002) and U.S. Pat. No. 8,003,346). In one embodiment, the DNA clamp may be mutated so it does not interact with DNA polymerase because it is being used as a passive clamp to hold the top and bottom strands together. After annealing, a proteinaceous clamp can be removed, e.g., using a protease.

In one embodiment, the DNA clamp used has sequence of at least 100 amino acids (e.g., up to 200 or 300 amino acids) that at least 80% identical (at least 90%, at least 95% or 99% or 100% identical) to the amino acid sequence of a wild type DNA clamp protein.

As noted above, the labeled oligonucleotide may comprise an affinity tag, e.g., a biotin moiety, or an optically detectable label such as a fluorescent label. In embodiments in which the labeled oligonucleotide contains an affinity tag, the method may further comprise contacting the D-loop-containing product with a solid support comprising a surface tethered capture agent for the affinity tag, thereby binding the D-loop-containing product to the solid support and isolating the D-loop-containing product from other nucleic acids in the sample. The efficiency of this step may be increased by using more than one (e.g., 2, 3, 4, 5 or 10 or more) labeled oligonucleotides. In these embodiments, because the target DNA is double stranded, both the top and bottom strands may be targeted by hybridization probes. It is also possible to target both the top and bottom strands with a single oligonucleotide, as illustrated in FIG. 7. In this scheme, it may be advantageous to use modified nucleotides such as unstructured nucleic acid bases or LNAs to decrease the hybridization probe's ability to bind to itself, and to increase the stability of the probe-target complex. Further, if it is critical to capture a single haplotype of a long sequence (such as a single gene) sequences on either end of the targeted gene could be selected. DNA fragments containing both end sequences should be captured more efficiently than broken DNAs containing only one of the targeted sequences.

In some embodiments, the labeled oligonucleotide may hybridize to both strands of the double stranded DNA molecule, and the method further comprises supercoiling the D-loop-containing product after it is isolated. In these embodiments, DNA condensation may reduce the volume of captured large DNA fragments, reducing the hydrodynamic shear forces on the DNA, and thus reducing the probability of DNA strand breakage. This step of the method may be done by any convenient method. Exemplary DNA condensation methods may polyvalent cations (Todd et al, Nucleic Acids Res. 2008 36:501-10), surfactants (Hays et al, Langmuir. 2007 23:5609-14), peptides (Saccardo et al, Adv. 2009 27:432-8), organic solvents (Ke PLoS One. 2010 5:e13308) and protein binding (Belmont et al, Curr Opin Cell Biol. 2006 18:632-8).

If two or more regions on a DNA strand are fixed to a surface or to one another, a topologically distinct domain is created, and the DNA in the domain can be over- or underwound (resulting in supercoiling). As an example, unwinding one region of a linear DNA creates no supercoiling, as the DNA can freely rotate. In a covalently closed circular DNA, unwinding of one region necessarily results in overwinding of another region; this is often expressed as a writhe of one duplex around another. DNA from cells is typically underwound (negatively supercoiled), such that covalently closed circular DNA is usually supercoiled around itself. Supercoiled DNA is more compact, and thus will be less susceptible to shear forces in solution.

Figure 3:
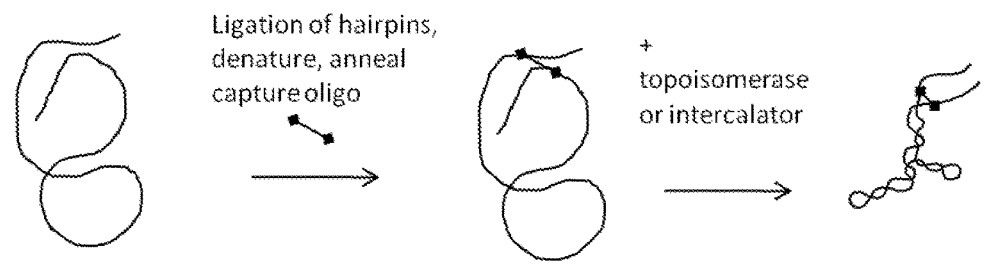
FIG. 3 schematically illustrates an embodiment that includes bidentate capture and topological condensation.
Figure 8:
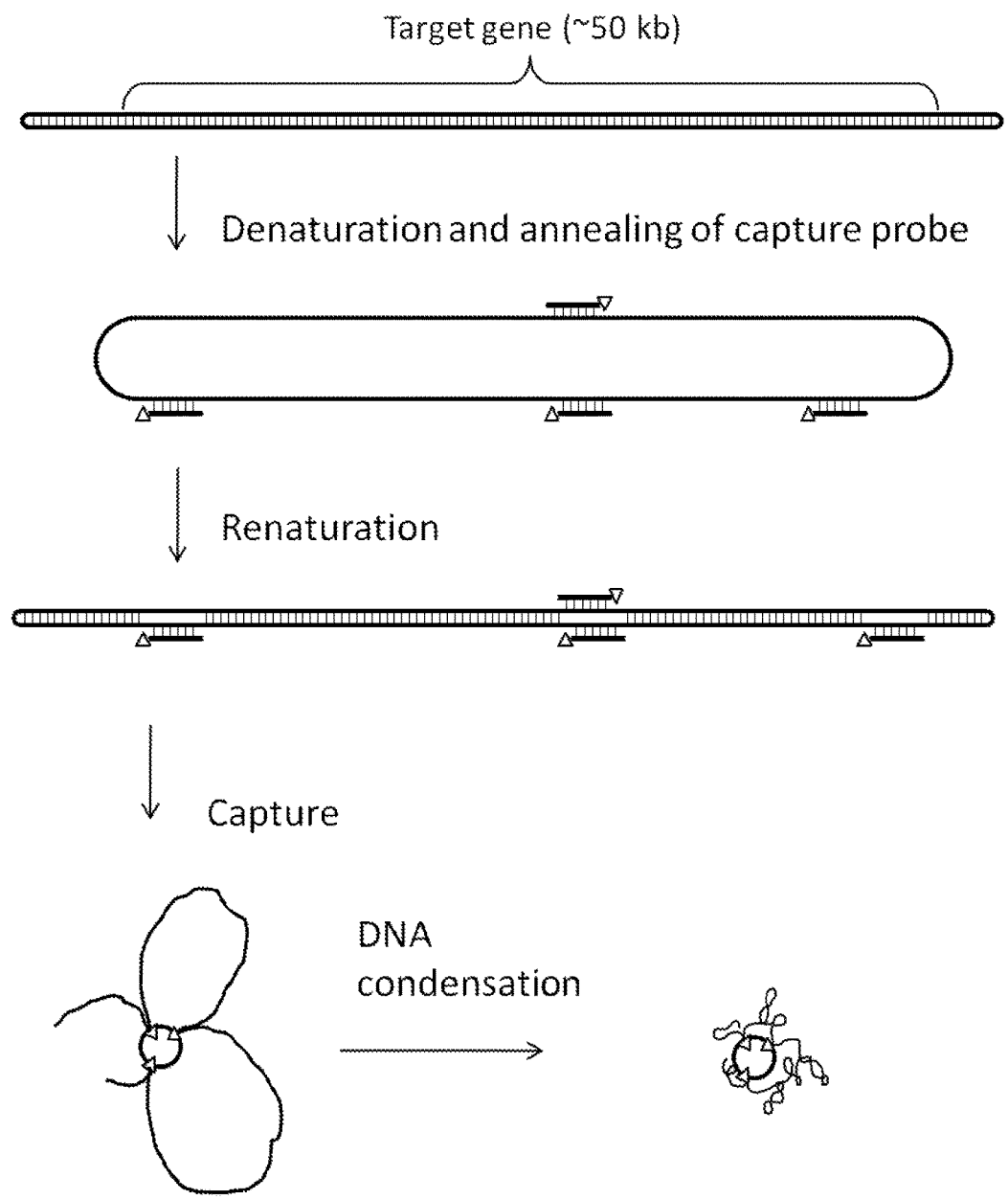
FIG. 8 schematically illustrates an embodiment in which a double stranded DNA molecule is captured using a multiple capture oligonucleotides, and the captured molecule is condensed.

In one embodiment, a bidentate capture oligo that binds to two different sequences or a pair of capture oligos bound to two different sequences can be used to create a topologically closed domain, and this domain can be supercoiled by a topoisomerase (e.g., a DNA gyrase to induce (−) supercoils or a reverse gyrase to induce (+) supercoils) or by the addition of chemicals such as intercalators such as chloroquine or minor groove binders such as netropsin (see, e.g., FIG. 3). One target DNA may be targeted with two capture oligos, creating a single topological domain between the oligos, or it may be targeted by more than two capture oligos, creating two or more domains. The capture oligos may target the same strand (e.g., the top strand) or they may target different strands (e.g., the top and the bottom strand.) Supercoiling may promotes disentanglement (unknotting and decatenation), so individual DNAs can be isolated without being linked to other DNAs. Further, supercoiling should not inhibit most enzymatic processes, and it is readily reversible by introducing a nick or break. Therefore, the compacted DNA may be used directly in a downstream reaction (e.g., synthesis involving a polymerase), or it could be easily "unpacked" for analysis after the capture step. In a particular embodiment and as illustrated in FIG. 8, a target nucleic acid can be targeted using several labeled oligonucleotides that contain affinity tags, then bound to a solid support that using the affinity tags, supercoiled, and then isolated from non-target nucleic acids. Addition of the supercoiling step during isolation may improve the yield of long molecules, and it may improve the specificity of capture by ensuring that multiple sites are bound by capture oligos.

After the D-loop-containing product is isolated, it may be genotyped. In particular embodiments, the double stranded DNA may be sequenced. In certain embodiments, isolated product may contain sequences that are compatible with use in, e.g., Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol. Biol. 2009; 553:79-108); Appleby et al (Methods Mol. Biol. 2009; 513:19-39) and Morozova (Genomics. 2008 92:255-64), which are incorporated by reference for the general descriptions of the methods and the particular steps of the methods, including all starting products, reagents, and final products for each of the steps. In one embodiment, the isolated product may be sequenced using nanopore sequencing (e.g. as described in Soni et al Clin Chem 53: 1996-2001 2007, or as described by Oxford Nanopore Technologies). Nanopore sequencing is a single-molecule sequencing technology whereby a single molecule of DNA is sequenced directly as it passes through a nanopore. A nanopore is a small hole, of the order of 1 nanometer in diameter. Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence. Nanopore sequencing technology as disclosed in U.S. Pat. Nos. 5,795,782, 6,015,714, 6,627,067, 7,238,485 and 7,258,838 and U.S. Pat Appln Nos. 2006003171 and 20090029477.

The method described above may also be used in to study DNA methylation at the sequence level. Such methods are typically done by treating a target nucleic acid with sodium bisulfite. However, bisulfite modification can thwart hybridization-based approaches, because the modification changes the sequence of the unmethylated cytosines, creating an unknown number of mismatches with hybridization probes. Although the bisulfite sequence modification of constitutively methylated or unmethylated sequences can be predicted, these regions may be less relevant to biological research than partially methylated sequences (e.g., the "CpG shores".) Capture of longer DNA sequences allows the capture probes to bind sequences adjacent to the target region where the methylation level may be unknown or dynamically changing. A second issue with bisulfate modification of DNA is that the DNA is usually denatured during the treatment. Use of the method described above should address this issue, as the DNA could be renatured after the bisulfate treatment, and the resulting duplex DNA will be more stable for isolation and downstream analysis.

The method described above can also be used for long-range haplotyping by using hemizygous deletions to differentially label maternal and paternal chromosomes. The method may be employed to capture such hemizygous sequences together with adjoining sequence. In this way, maternal and paternal copies of DNA could be separated and analyzed independently. This would enable haplotype phased sequencing.

Finally, one could use the method described above (particularly the hairpin ligation method) to purify long DNA fragments made by ligation of shorter DNA oligonucleotides. If a ligation were done connecting a number of double-stranded DNA fragments, hairpins with staggered ends complementary to the ends of the desired full-length synthetic ligated fragment could be added on with DNA ligase. Subsequent treatment of the synthetic mixture with an exonuclease that chews back from single-stranded DNA ends would destroy any synthetic fragments that did not have hairpins ligated on to both of their ends, and thus were not full-length.

Figure 5:
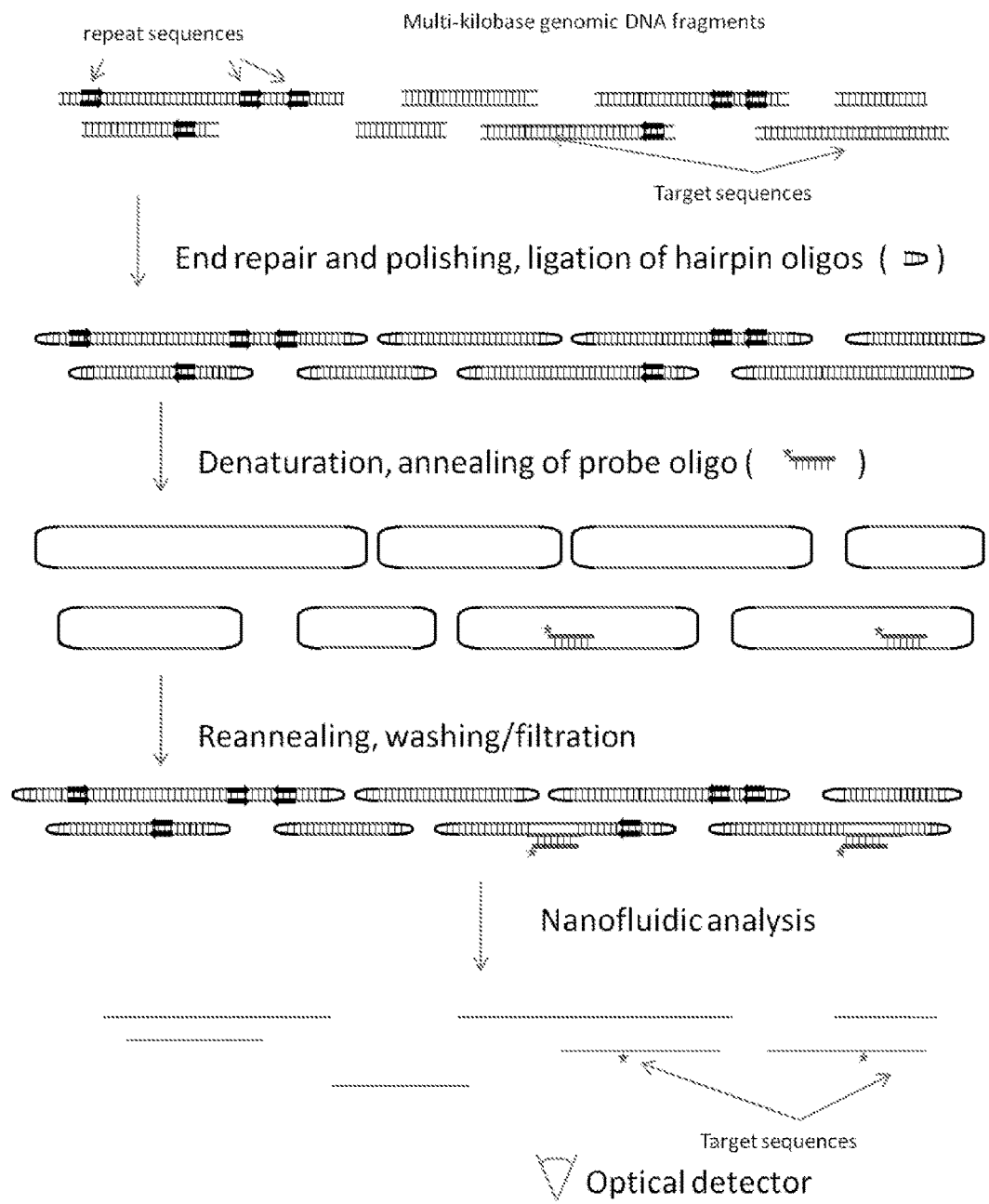
FIG. 5 schematically illustrates an embodiment of the method that uses optically detectable labeled oligonucleotides.

In embodiments in which the labeled oligonucleotide contains a labeled nucleotide, the method may further comprise subjecting the D-loop containing product to microfluidic analysis. FIG. 5 schematically one embodiment of this method. For example, the D loop containing product may be stretched as it flows through a nanofluidic channel. In these embodiments, the nanofluidic channel may have a diameter of less than 200 nm, for example, less than 150 nm, less than 100 nm, less than 50 nm, or less than 20 nm. The confinement of the DNA molecules in the nanochannels leads to elongation of the DNA molecules, allowing optical interrogation. See e.g., Tegenfeldt et al (2004) *Proc. Nat. Acad. Sci. USA* 101:10979-10983; and Douville et al. (2008) *Anal. Bioanal. Chem.* 391:2395-2409. Details of using microfluidic channel to stretch and analyze single molecules may be found in US Pat Pub 20080239304 and US20080213912, disclosures of the patent publications are incorporated herein by reference. In these embodiments, after denaturation, certain sequences would be expected to form other secondary structure, and repeat sequences from mismatched segments of DNA will anneal to one another. Use of the method described above may allow more efficient reannealing of denatured DNA, and the reannealed (double stranded) DNA can now be analyzed in nanofluidic channels. In certain embodiments, this should allow the hybridization of a fluorescently labeled probe to a specific sequence, enabling sequence analysis of large DNA fragments (FIG. 5).

A composition produced by the method described above is also provided. This composition comprises a D-loop containing product comprising a double stranded DNA molecule in which the top and bottom strands are clamped together, and a labeled oligonucleotide annealed a sequence in the double stranded DNA molecule. The composition may be in any form, e.g., dried or in an aqueous environment, in any volume, e.g., of 5 µl to 200 µl for example. Further details of the molecules that may be found in the composition are described in the methods section above. In particular embodiments, the labeled oligonucleotide of the D-loop containing product is not extendible by a polymerase, and not capable of being used as a substrate for rolling-circle replication because of a covalent or non-covalent modification that prevents a polymerase from displacing the strands.

The method described above can be employed to manipulate and analyze double stranded DNA from virtually any nucleic acid source, including but not limited to genomic DNA and complementary DNA, plasmid DNA, mitochondrial DNA, synthetic DNA, and BAC clones etc. Furthermore, any organism, organic material or nucleic acid-containing substance can be used as a source of nucleic acids to be processed in accordance with the present invention including, but not limited to, plants, animals (e.g., reptiles, mammals, insects, worms, fish, etc.), tissue samples, bacteria, fungi (e.g., yeast), phage, viruses, cadaveric tissue, archaeological/ancient samples, etc. In certain embodiments, the double stranded DNA used in the method may be derived from a mammal, where in certain embodiments the mammal is a human.

In certain embodiments, the double stranded DNA being analyzed may be derived from a single source (e.g., a single organism, virus, tissue, cell, subject, etc.), whereas in other embodiments, the nucleic acid sample may be a pool of nucleic acids extracted from a plurality of sources (e.g., a pool of nucleic acids from a plurality of organisms, tissues, cells, subjects, etc.), where by "plurality" is meant two or more. As such, in certain embodiments, a nucleic acid sample can contain nucleic acids from 2 or more sources, 3 or more sources, 5 or more sources, 10 or more sources, 50 or more sources, 100 or more sources, 500 or more sources, 1000 or more sources, 5000 or more sources, up to and including about 10,000 or more sources. Molecular barcodes may allow the sequences from different sources to be distinguished after they are analyzed.

KITS

Also provided by this disclosure are kits for practicing the subject methods, as described above. The subject kits contain at least: a) reagents for clamping the top and bottom strands of a double stranded DNA molecule; and b) a labeled oligonucleotide, wherein the labeled oligonucleotide is complementary to a sequence of nucleotides in the double stranded DNA molecule. The kit may optionally contain other components, for example: reagents for fragmenting genomic DNA, hybridization reagents, capture buffer, a binding partner for labeled oligonucleotide, where the binding partner is linked to a solid support, etc. The various components of the kit may be present in separate containers or certain compatible components may be precombined into a single container, as desired.

In addition to above-mentioned components, the subject kits may further include instructions for using the components of the kit to practice the subject methods, i.e., to instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

The invention claimed is:

1. A method comprising:
   a) clamping the top and bottom strands of a double stranded DNA molecule to produce a duplex in which the top and bottom strands are linked;
   b) denaturing the duplex to produce a denatured product; and
   c) renaturing the denatured product in the presence of a labeled oligonucleotide, wherein the labeled oligonucleotide hybridizes to a sequence of nucleotides on one strand in the double stranded DNA molecule, thereby producing a renatured, double-stranded product that comprises a triplex region comprising the labeled oligonucleotide.

2. The method of claim 1, wherein the clamping step comprises covalently linking the top and bottom strands of the double stranded DNA molecule to produce a duplex in which the top and bottom strands are covalently linked.

3. The method of claim 2, wherein the covalently linking is done by ligating a hairpin adaptor to one or both ends of the double stranded DNA.

4. The method of claim 3, wherein the hairpin adaptor comprises a hairpin region that has a $T_m$ over 70° C.

5. The method of claim 2, wherein the covalently linking is done by ligating a double stranded adaptor to one or both ends of the double stranded DNA, and covalently crosslinking the top and bottom strands of the double stranded adaptor.

6. The method of claim 2, wherein the covalently linking is done by ligating two molecules of a hairpin adaptor to the double stranded DNA, and wherein the hairpin adaptor comprises a nucleotide sequence that produces a restriction site if an adaptor dimer is produced.

7. The method of claim 1, wherein the labeled oligonucleotide comprises an affinity tag.

8. The method of claim 7, wherein the affinity tag is a biotin moiety.

9. The method of claim 7, further comprising:
d) contacting the renatured, double-stranded product of step (c) with a solid support comprising a surface tethered capture agent for the affinity tag, thereby binding the renatured, double-stranded product to the solid support and isolating the renatured, double-stranded product from other nucleic acids in the sample, thereby producing an isolated renatured double-stranded product.

10. The method of claim 9, wherein the method comprises genotyping the double stranded DNA molecule in the isolated renatured double-stranded product.

11. The method of claim 9, wherein in step (c) the labeled oligonucleotide hybridizes to more than one region of the double stranded DNA molecule to produce a topologically distinct region, and the method comprises supercoiling the renatured product after it is contacted with the solid support.

12. The method of claim 9, wherein the covalently linking is done by ligating an adaptor to the double stranded DNA, wherein the adaptor comprises at least one cleavable linkage so that it can be removed from the renatured product after the renatured product has been isolated.

13. The method of claim 9, wherein step (c) further comprises renaturing the denatured product in the presence of multiple different labeled oligonucleotides, wherein the multiple different labeled oligonucleotides hybridize to different sequences of nucleotides in the double stranded DNA molecule.

14. The method of claim 1, wherein the labeled oligonucleotide comprises an optically detectable label.

15. The method of claim 1, wherein the labeled oligonucleotide is made of locked nucleic acid (LNA) or unstructured nucleic acid (UNA).

16. The method of claim 1, wherein the method does not comprise studying DNA methylation, and the denatured product of step (c) is not bisulfite-treated.

17. The method of claim 1, wherein the double stranded DNA molecule of (a) is in the range of 20-200 kb in length.

* * * * *